US008650959B2

(12) United States Patent
De Odorico et al.

(10) Patent No.: US 8,650,959 B2
(45) Date of Patent: Feb. 18, 2014

(54) PLANAR PROBE HEAD AND ULTRASONIC TESTING DEVICE AND METHOD FOR A COMPONENT

(75) Inventors: Walter Franz De Odorico, Bayern (DE); Roman Heinrich Koch, Bayern (DE); Wolfgang Haase, Bayern (DE)

(73) Assignee: GE Sensing & Inspection Technologies (DE)

( * ) Notice: Subject to any disclaimer, the term of this patent is extended or adjusted under 35 U.S.C. 154(b) by 232 days.

(21) Appl. No.: 13/127,430

(22) PCT Filed: Nov. 3, 2009

(86) PCT No.: PCT/EP2009/064564
§ 371 (c)(1),
(2), (4) Date: Aug. 2, 2011

(87) PCT Pub. No.: WO2010/060759
PCT Pub. Date: Jun. 3, 2010

(65) Prior Publication Data
US 2011/0283799 A1   Nov. 24, 2011

(30) Foreign Application Priority Data
Nov. 3, 2008  (DE) .......................... 10 2008 037 516

(51) Int. Cl.
*G01N 29/28*   (2006.01)
(52) U.S. Cl.
USPC ............................................. 73/644; 73/661
(58) Field of Classification Search
USPC ......... 73/661, 649, 658, 643, 644, 632, 866.5
See application file for complete search history.

(56) References Cited

U.S. PATENT DOCUMENTS

| 4,165,649 A | | 8/1979 | Greer, Jr. | |
|---|---|---|---|---|
| 4,472,975 A | * | 9/1984 | Beck et al. | 73/644 |
| 5,123,281 A | * | 6/1992 | Cox et al. | 73/644 |
| 5,228,343 A | * | 7/1993 | Schoenen et al. | 73/644 |
| 5,469,744 A | * | 11/1995 | Patton et al. | 73/644 |

(Continued)

FOREIGN PATENT DOCUMENTS

FR            2891910 A      4/2007

OTHER PUBLICATIONS

International Search Report from corresponding application No. PCT/EP2009/064564 dated Jul. 30, 2010.

*Primary Examiner* — Helen Kwok
(74) *Attorney, Agent, or Firm* — Global Patent Operation; Mark A. Conklin (57) ABSTRACT

A planar probe for the coupling of ultrasonic signals to a planar component to be tested by means of water-free jet technology is provided. The planar probe includes: at least one preflow chamber; a flow chamber located downstream of at least one preflow chamber, wherein the flow chamber extends through a slot-shaped water outlet opening to a lower surface of the planar probe; a probe, wherein a lateral surface of the probe comprises emitting/receiving elements and forms an inner wall section of the flow chamber; a base body for the reception of the probe; and a sliding plate comprising the slot-shaped water outlet opening, whose planar extension along the component is larger than the planar extension of the base body along the component, wherein the planar probe is connected to the sliding plate.

19 Claims, 6 Drawing Sheets

(56) References Cited

U.S. PATENT DOCUMENTS

| | | |
|---|---|---|
| 5,567,881 A | 10/1996 | Myers |
| 6,298,727 B1 * | 10/2001 | Fleming et al. .................. 73/644 |
| 7,021,143 B2 * | 4/2006 | Dasch ............................. 73/620 |
| 7,151,645 B2 * | 12/2006 | Won et al. .................. 360/77.04 |
| 7,275,437 B2 * | 10/2007 | Bukin ............................. 73/597 |
| 7,284,434 B1 | 10/2007 | Fleming |
| 7,637,163 B2 * | 12/2009 | Fetzer et al. .................... 73/644 |
| 7,798,003 B2 * | 9/2010 | Maurer et al. .................. 73/644 |
| 8,087,298 B1 * | 1/2012 | DiMambro et al. ............ 73/629 |
| 8,336,384 B2 * | 12/2012 | Fetzer et al. .................... 73/644 |
| 2005/0132809 A1 | 6/2005 | Fleming |
| 2007/0175282 A1 * | 8/2007 | Fetzer et al. .................... 73/649 |

\* cited by examiner

Fig. 8 and is arranged above a tapered flow chamber. The tapered flow chamber forms a slot for a liquid coupling medium between the linear array transducer and the structure to be tested, if the linear array transducer is positioned over an edge of the structure. A lower surface of the flow chamber lies directly on the surface of the structure to be tested. Also, the planar probe is attached pivotably to a retainer around its longitudinal axis.

PLANAR PROBE HEAD AND ULTRASONIC TESTING DEVICE AND METHOD FOR A COMPONENT

BACKGROUND OF THE INVENTION

1. Field of the Invention

Embodiments of the present invention relate to a planar probe for the coupling of ultrasonic signals to a planar component to be tested by means of water jet technology.

2. Description of the Prior Art

A planar probe of the type mentioned at the outset is described in WO-A-2008/106535. The planar probe is particularly designed for testing the edges of a structure and comprises a linear array transducer, which is connected with a housing and is arranged above a tapered flow chamber. The tapered flow chamber forms a slot for a liquid coupling medium between the linear array transducer and the structure to be tested, if the linear array transducer is positioned over an edge of the structure. A lower surface of the flow chamber lies directly on the surface of the structure to be tested. Also, the planar probe is attached pivotably to a retainer around its longitudinal axis.

A modular design of an ultrasonic probe is known from EP-A-0 164 168, which can be coupled to a component to be tested by means of water jet technology.

In the case of this embodiment the flow chamber tapers in the direction of a slot-shaped water outlet opening, so that a lower surface of the flow chamber has a small surface area.

U.S. Pat. No. 4,507,969 relates to an ultrasonic liquid jet probe. This probe also comprises a preflow chamber with at least one water inlet, as well as one flow chamber downstream of at least one water outlet opening. The flow chamber is designed on the outside surface in the shape of a truncated cone, in which the lower surface is designed as a circular surface.

In U.S. Pat. No. 7,234,353 a fluidless acoustic coupling of an ultrasonic sensor for the testing of an internal structure of a component is described. An ultrasonic transducer is thereby positioned by means of an automatic positioning device such as a controllable handling device.

A further ultrasonic probe arrangement is described, for example, in WO 2006/122798 A1. This comprises preflow and filter chambers, which overflow into a jet nozzle, in which a probe is enclosed by the preflow or filter chambers and flowed around by water.

The arrangement is indeed characterized by excellent flow properties; however, the replacement of the probe is expensive and connected with the disassembly of the filter or preflow chambers.

For certain applications, for example, the ultrasonic testing of planar components such as plates, in which the probe arrangement rests on the upper surface of the planar component to be tested and is moved along it, the weight of the probe also is of significance, so that there is a need for a probe arrangement with low weight and good sliding properties.

Based on this, the task, which underlies embodiments of the present invention, is to further develop a planar probe of the type mentioned at the outset, so that the ultrasonic testing of planar components can be simplified.

SUMMARY OF THE INVENTION

In one embodiment, a planar probe for the coupling of ultrasonic signals to a planar component to be tested by means of water jet technology is provided. The planar probe comprises: at least one preflow chamber with at least one water inlet; a flow chamber located downstream of at least one preflow chamber, wherein the flow chamber extends through a slot-shaped water outlet opening to a lower surface of the planar probe; a probe detachably arranged outside of at least one of the flow chamber and the preflow chambers in a freely accessible manner, wherein a lateral surface of the probe comprises emitting/receiving elements and forms an inner wall section of the flow chamber a base body for the reception of the probe; and a sliding plate comprising the slot-shaped water outlet opening, the sliding plate forming a lower surface of the planar probe on the component side, whose planar extension along the component is larger than the planar extension of the base body along the component, wherein a waterflow forms between the lower surface of the planar probe and a surface area of the component to be tested, and wherein the planar probe is connected to the sliding plate.

In an alternate embodiment, a device for the ultrasonic testing of a planar component by means of water jet technology is provided. The device comprises: a planar probe comprising: at least one preflow chamber with at least one water inlet; a flow chamber located downstream of at least one preflow chamber, wherein the flow chamber extends through a slot-shaped water outlet opening to a lower surface of the planar probe; a probe detachably arranged outside of at least one of the flow chamber and the preflow chambers in a freely accessible manner, wherein a lateral surface of the probe comprises emitting/receiving elements and forms an inner wall section of the flow chamber, a base body for the reception of the probe; and a sliding plate comprising the slot-shaped water outlet opening, the sliding plate forming a lower surface of the planar probe on the component side, whose planar extension along the component is larger than the planar extension of the base body along the component, wherein a waterflow forms between the lower surface of the planar probe and a surface area of the component to be tested, and wherein the planar probe is connected to the sliding plate, wherein the planar probe can be combined with a handling machine via a a holding device and swivel-mounted in the holding device around the axis running transversely to the test direction and wherein the planar probe can be moved along the component in the test direction, wherein the sliding plate projects above the base area of the base body, and wherein the planar probe glides on a water-sliding cushion farmed between the lower surface of the sliding plate and the surface area of the component.

In an alternate embodiment, a method for testing a component having planar production-related through holes by means of coupling of ultrasonic signals by water jet technology using a planar probe is provided. The planar probe may be connected with a sliding plate, whose planar extension is designed in such a manner that its breadth has an extension transverse to the test direction, which is larger than the usual extension of the production-related through holes and/or has an extension in the test longitudinal direction, which is larger than the usual extension of the production-related through holes.

BRIEF DESCRIPTION OF THE DRAWINGS

Further particulars, advantages and characteristics of the embodiments of the present invention result not only from the claims, the characteristics to be learned from these, in themselves and/or in combination, but rather also from the following description of the embodiments to be learned from the drawings, in which;

DETAILED DESCRIPTION OF THE INVENTION

Figure 1:
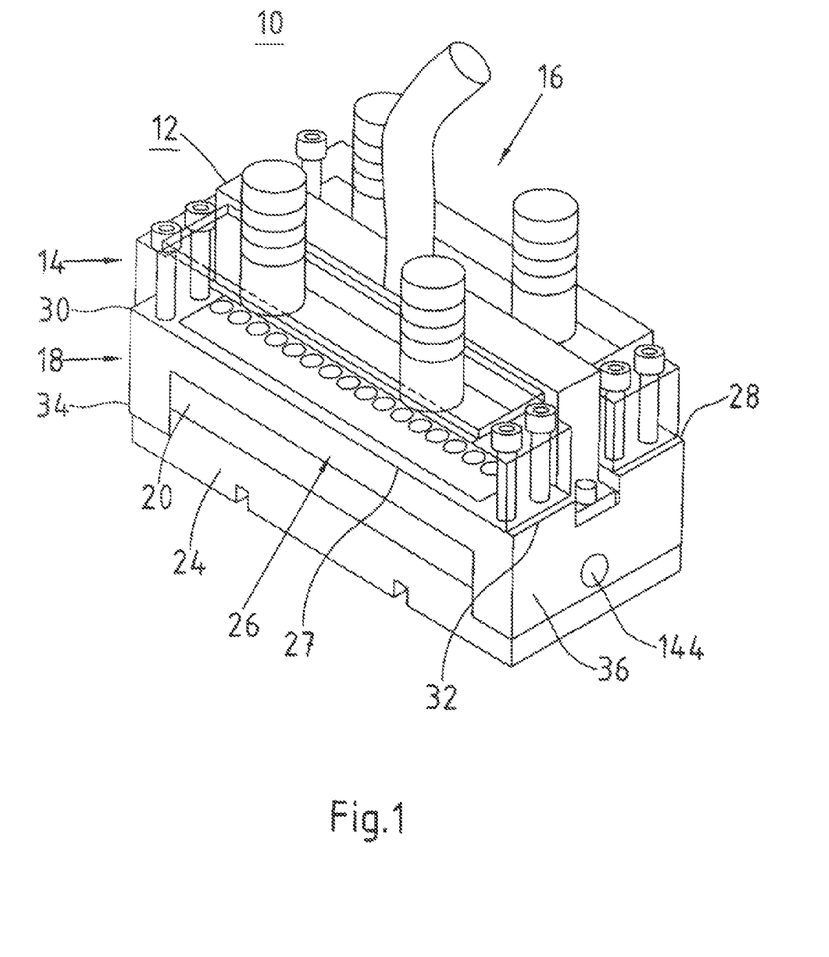
FIG. 1 shows a three-dimensional representation of the probe arrangement.

FIG. 1 shows a three-dimensional view of a probe arrangement 10 according to the present invention, which in the present case is designed as a planar probe. The probe arrangement 10 has a modular design, comprising a probe 12, two preflow chambers 14, 16, a base body 18, two flow chamber elements 20, 22 as well as a sliding plate 24.

The base body 18 is preferably constructed from a metallic material such as brass. The base body 18 has an essentially rectangular base plate 26, with longitudinal edges 27, 28, which are designed longer compared to transverse edges 30, 32. The side-wall elements 34, 36, which are designed shorter compared to a longitudinal extension of the base plate 24, extend from the shorter transverse edges 30, 32.

Figures 2, 3:
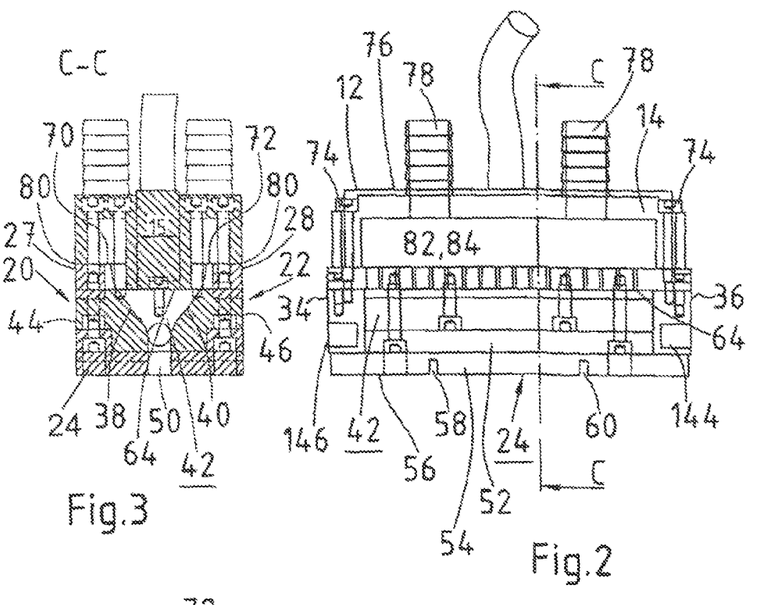
FIG. 2 shows a sectional representation according to FIG. 1.
FIG. 3 shows a lateral view of the probe arrangement.

It can be learned from FIGS. 2 and 3, that the flow chamber elements 20, 22, whose respective inner surfaces 38, 40 jointly form an essentially funnel-shaped contour of a flow chamber 42, extend between the side-wall elements 34, 36. The outer sides 44, 46 of the flow chamber elements 20, 22 are flush with longitudinal edges 27, 28 of the base plate 26.

The flow chamber elements 20, 22 are fixed via the sliding plate 24 to the base body 18. The sliding plate 24 has a slot-shaped opening 50 which forms the water outlet.

The sliding plate 24 is designed as a plastic molded part and comprises a first upper section 52, which extends between the side-wall elements 34, 36 and lies closely against the latter, as well as a lower section 54 which has at least the surface area of the base plate 26.

To prevent a water pressure overload between sliding plate 24 and the component to be tested, slots 58, 60 are introduced on a lower surface 56 of the sliding plate 48.

Figure 4:
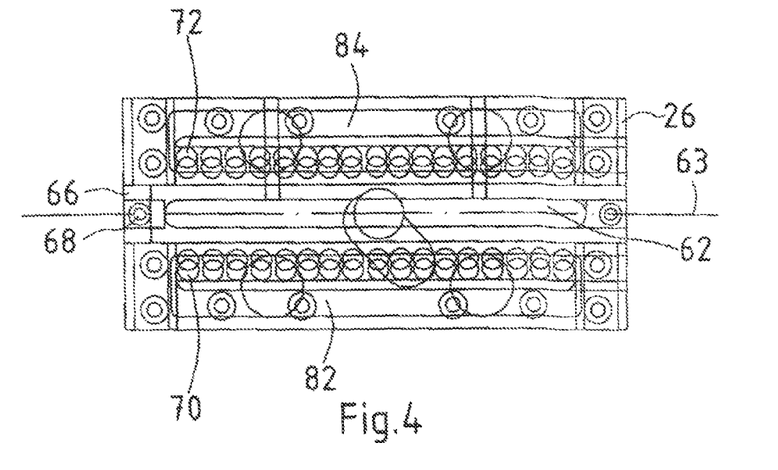
FIG. 4 shows a top view of the probe arrangement according to FIG. 1.

Along a longitudinal center line 62 of the base plate 26, a slot-shaped opening is introduced, over which also aligned in longitudinal direction, the probe 12 is arranged, as illustrated in FIG. 4. In this respect, a lower surface 64 of the probe 12 forms a section of a wall of the flow chamber 42. The probe 12 is arranged in a groove 66 running along the slot-shaped opening 62 and is screwed together with the base body 18 via fastening elements such as the screws 68. The through holes 70, 72 arranged at both sides in a series, such as boreholes extending into the flow chamber 42, run parallel to the slot-shaped opening 62. Over the through holes 70, 72, in each case, one of the preflow chambers 14, 16 is arranged, which extend parallel to the probe 12 and are connected with the base plate 26 via fastening elements 74 such as screws.

The preflow chambers 14, 16 are also designed from plastic molded parts and have connections 78 on their upper surface 76, to which water inlets can be connected. A milled-out portion is introduced in the lower surface 80 of the preflow chamber elements 14, 16, which forms a chamber space 82, 84. The through holes 70, 72 in each case open out into one of the chamber spaces 82, 84.

Figure 5:
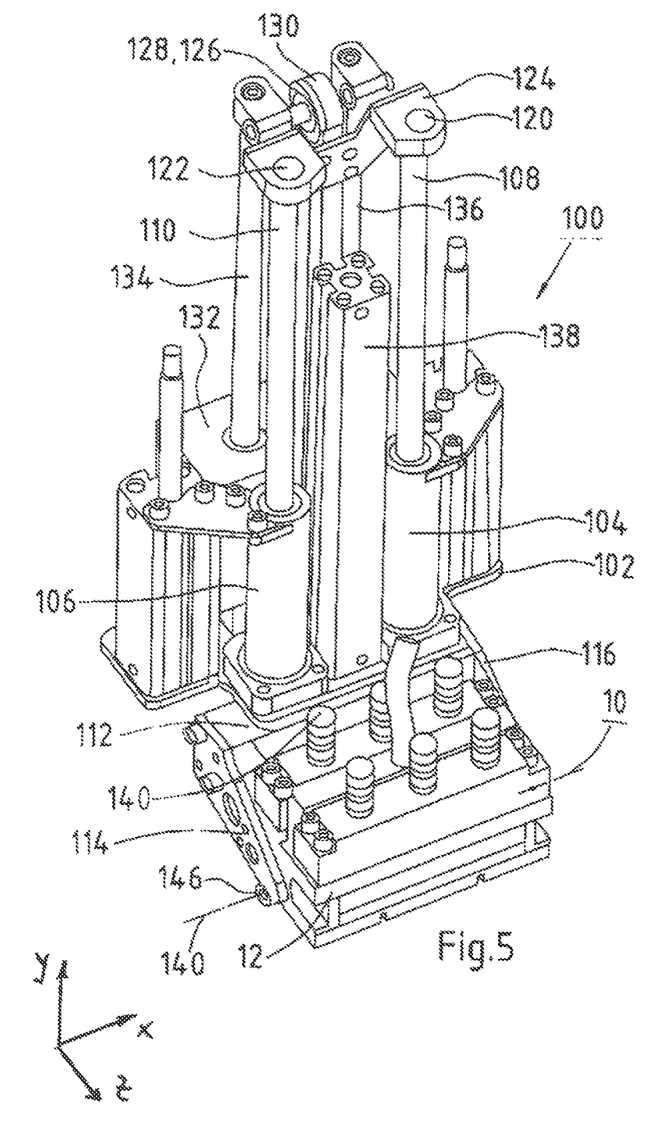
FIG. 5 shows a three-dimensional representation of a gravitation-compensating device.

In the case of a fully automated ultrasonic testing of planar components, the probe 10 designed as a planar probe is operated in a gravitation-compensating device 100 according to FIG. 5. The gravitation-compensating device comprises a basis plate 12, which can be firmly combined with a handling device such as a gantry robot (not depicted). From an upper surface of the basis plate 102, the guide cylinders 104, 106, which are arranged spaced parallel to each other, are extending. In the guide cylinders 104, 106, guide rods 108, 110 are mounted, so that they can be displaced axially. First, the lower ends of the guide rods 110, 108, which extend underneath the base plate 102, are interlinked via a connecting block 112. From the connecting block, holding elements 114, 116, which hold the probe 10 in operating position, go out. In the process, the holding elements 114, 116 can be combined, such as screwed together, with the base body 12 of the probe arrangement 10.

Second, the upper ends 120, 122 of the guide rods 110, 108, which extend above the base plate, are also connected with each other via a connector element 124. The connector element 124 is connected with a closed strip 130, which is guided via a first guide roller 126 and a second guide roller 128 (not depicted). Also, the strip 130 is coupled with a gravitation counterweight 132, which is guided in a slidable manner along the guide rods 134, 136 opposite to the motion of the probe 10. The ends of the guide rods 134, 136 are connected with each other via an axle, on which the first guide roller 126 is mounted circumferentially in a rotating position between the guide rods. The second guide roller 128 is mounted in a rotation position in the base plate 102.

Furthermore, a pneumatic cylinder 138 is provided on the base plate 100, preferably between the guide rods 110, 108, in which a plunger rod 140 of the pneumatic cylinder 138 is connected with the connecting block 112, in order to adjust the probe 10 in operating position.

Reference is subsequently made to the Cartesian coordinate system depicted in FIG. 5. The probe arrangement 10 arranged between the holding elements 114, 116 is pivotally mounted around an axis 140 running along the X-axis of the coordinate system, i.e. transversely to the direction of motion (Z-axis). For this purpose, receptacles 142, 144 are introduced into the base body 18, in which in each case a pivot pin 146 is received, which can be connected with the holding element 114, 116. Thus, a cardan suspension is achieved, whereby the probe arrangement 10 can passively follow a contour of the part to be tested. According to the prior art, this was not possible, since the known probe arrangements are too heavy and inflexible.

Figure 6:
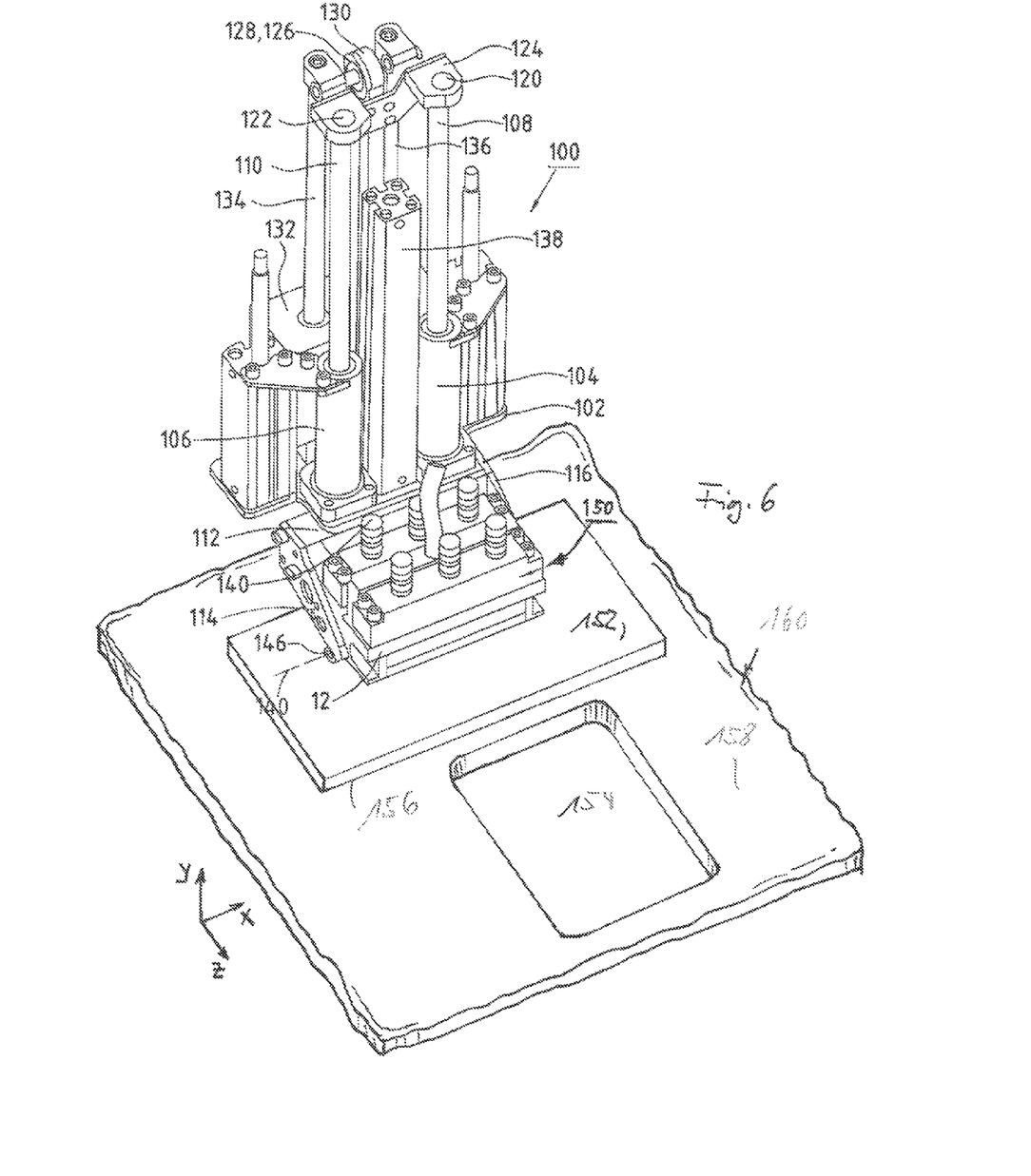
FIG. 6 shows a perspective representation of the planar probe with a sliding plate in the area of a through hole of the component to be tested.

FIG. 6 shows the gravitation-compensating device 100 with an embodiment of a planar probe 150, which differs from the embodiment according to FIGS. 1 to 5 in that a sliding plate 152 is provided, which has a surface area that is larger than the surface area of the base body (26). In particular, the sliding plate 52 has a dimensioning such that with the overrunning of a through hole 154 or an edge 156 at least one section of the lower surface 156 of the sliding plate 152 bears on the upper surface 158 of the component to be tested.

It is thereby ensured, that particularly when using the gravitation-compensating device 100 a bearing on the upper surface 158 of the component 160 is ensured and that a water cushion is always formed between the lower surface 156 of the sliding plate 152 and the upper surface 158.

In addition, through the extensive design of the sliding plate 152 it is achieved that with little water pressure a water cushion bearing the planar probe 150 is formed. In this connection, the grooves running on the lower surface 156 of the sliding plate arranged in the direction of travel as well as the turbulence-free flow, which are essentially formed through the multiplicity of openings between the preflow chamber and the flow chamber and ensure a uniform distribution of the water, have a supportive effect.

Compared to the prior art, i.e. planar probes with small bearing surfaces, which are not suitable for establishing a "water cushion," the planar probe in particular has the advantage, in conjunction with the gravitation-compensating device 100, that the test arrangement can be moved easily and thus more rapidly over the surface area, so that the test can be conducted more rapidly overall. In addition to this, based on the cardan suspension of the probe in conjunction with the gravitation-compensating device 100, the probe is movable in many degrees of freedom, so that unevennesses, convolutions and the like in the surface area 158 of the component to be tested can be compensated for, without, if need be, a reprogramming of the gantry robot guiding the arrangement that has to take place.

Figure 8:
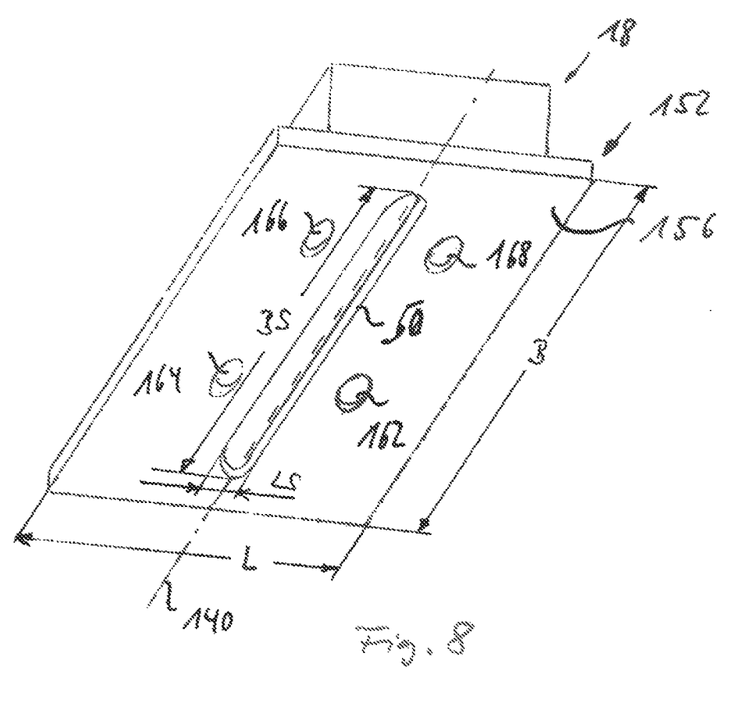
FIG. 8 shows a bottom view of the sliding plate.

FIG. 8 shows a perspective view of the lower surface 156 of the sliding plate 152. The slot-shaped water outlet opening 62 runs along the center axis 140, through which, on the one hand, ultrasonic waves are coupled via the waterflow to the component 160 to be tested and through which a waterflow is generated for the generation of a water cushion on which the sliding plate 152 bears. Additionally, water outlet openings 162, 164, 166, 168 are provided, through which water is streamed in between the lower surface 156 of the sliding plate and the surface area 158 of the component 160.

The water outlet openings 162-168 are connected via channels with the preflow chambers 14, 16.

Preferably, the sliding plate 152 has a length L in the test direction in the range of 100 mm≤L≤200 mm, preferably L=160 mm, and a breadth B transversely to the test direction in the range of 200 mm≤B≤300 mm, preferably B=230 mm. The slot-shaped water outlet opening 62 has an extension BS transversely to the test direction in the range of 50≤BS≤100 mm, preferably 75 mm, and an extension LS in the test direction in the range of 4 mm≤LS≤10 mm, preferably LS=6 mm.

It can be noted, regarding the dimensioning of the sliding plate 152, that the length L is larger than the maximum longitudinal extension of the through hole 154, and/or the breadth B is larger than the extension of the through hole 154 transversely to the test direction, so that in the case of the overrunning of the sliding plate 152 the latter bears with at least one section with the lower surface 156 on the surface area 158 of the component to be tested.

Figure 7:
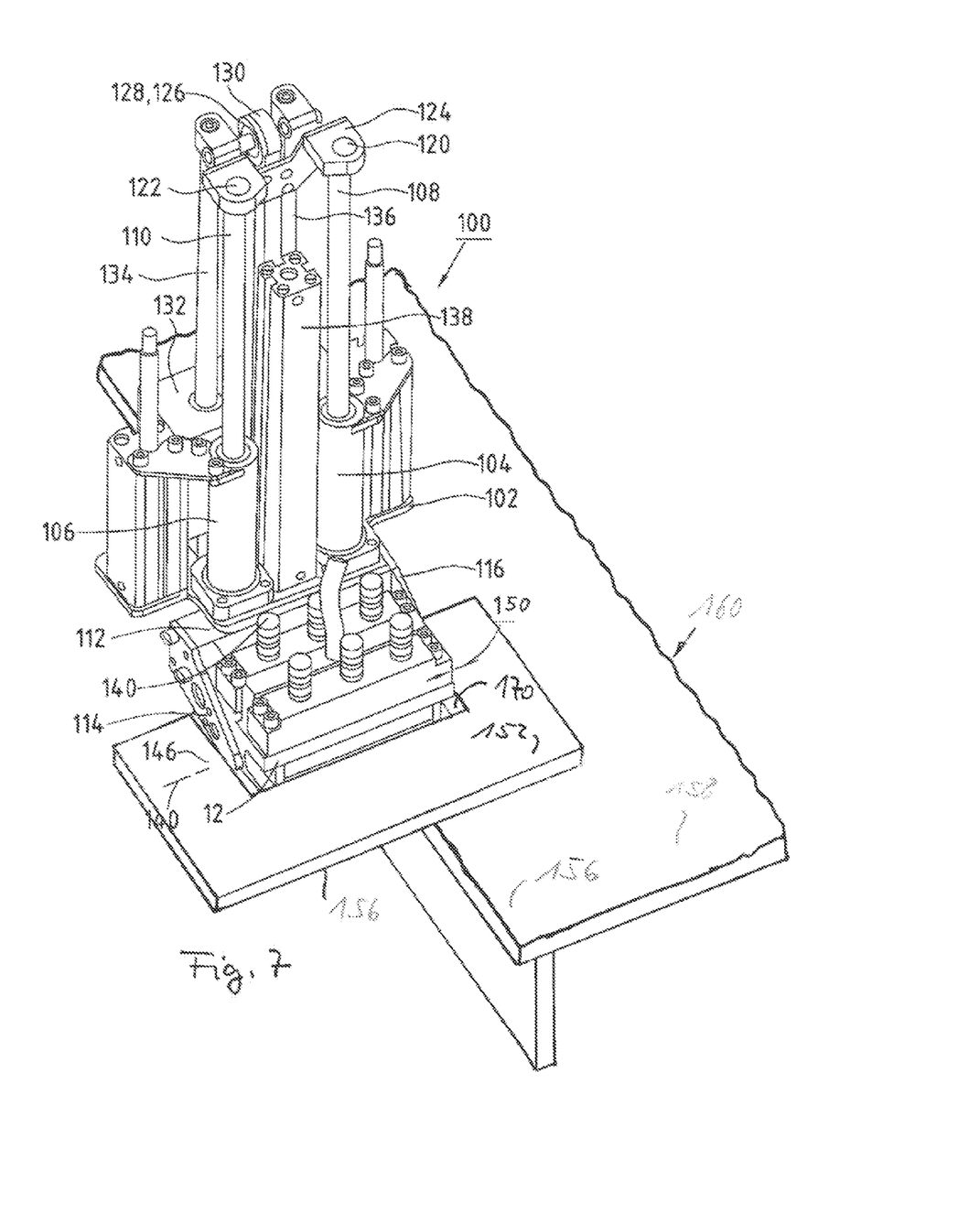
FIG. 7 shows a perspective representation of the planar probe with a sliding plate in the area of an edge of the component to be tested.

According to FIG. 7, the sliding plate 152 has a recess 170 on the top, in which the base body 12 is received with pivot pins 146. Thus, the distance of the rotational axis to the lower surface 156 of the sliding plate 152 is minimized in order to improve the swivel properties of the planar probe.

Compared to the prior art, advantages are attained as a result of the sliding plate with enlarged lower surface the bearing surface of the planar probe on a surface of the component to be tested is enlarged, whereby by using water jet technology a water cushion can be formed between the lower surface of the sliding plate and the surface of the component to be tested, on which the planar probe bears and is thus easily movable over the component to be tested.

Based on the large bearing surface, the use of the planar probe is possible together with a gravitation compensating device.

For the ultrasonic testing of planar components with production-related through holes, such as cut-outs or boreholes, the sliding plate projects above the base area of the base body and is larger in its dimensions than the size dimension of a through hole in the test direction and/or transverse to the test direction of the component to be tested.

The base body may be designed essentially in a U-shaped form, with a base plate, from which short sidewall elements extend to the opposite ends with respect to the length to the base plate, in which in the base plate, along its longitudinal axis, a slot-shaped opening may be introduced for the reception of the lower surface of the probe with emitting/receiving elements, as well as a series of through holes such as boreholes running on both sides parallel to the slot-shaped opening, in which a preflow chamber, which is independent and sealable against the upper surface of the base plate, is dedicated to each series of through holes, in which in each case intermediate elements forming an internal contour of the flow chamber are arranged between the sidewall elements along a lower surface of the base plate, and that the intermediate elements may be fixed over the sliding plate running parallel to the base plate and may be fastened to the base body.

Through the series of through holes arranged along the slot-shaped opening, a turbulence-free flow with a small water chamber may also achieved with this compact design.

Also, the design of the planar probe provides a simple design of the individual elements. Thus, changes can be implemented within a short period of time at low cost. The modular design simplifies the maintenance.

In one embodiment, the planar probe is arranged between the independently designed preflow chambers.

The preflow chambers may be shaped quadrangularly and consist of a plastic material, comprising a milling forming a chamber space, introduced on a lower surface, as well as at least one through hole installed in an upper surface for the reception of a water connection. The preflow chamber may be screwed in on the upper surface of the base plate via fastening elements, such as screws, so that boreholes running parallel to the slot-shaped opening open out into the chamber space of the preflow chamber.

In order to achieve a turbulence-free flow, the boreholes may be mounted in an angle bracket in the base plate of the base body, which essentially corresponds to the angle of inclination of the flow chamber contour in the area of the boreholes.

According to an alternate embodiment, the contour of the flow chamber may be formed by the two opposite intermediate elements. Thus, by means of replacement of the intermediate elements, a contour change of the flow chamber is possible in an easy manner, whereby the base body as well as the sliding plate and preflow chamber do not have to be replaced.

In order to avoid a dynamic pressure between the sliding plate and the component to be tested, it is provided that slot-shaped milled-out portions may be formed on a lower surface of the sliding plate facing the component to be tested.

Irrespective of this, an overflow valve may be arranged in a water supply conduit, so that excess water could be discharged before the preflow chamber.

Through the cardan suspension of the probe arrangement in the holding device, an advantage is achieved in that the probe arrangement can passively follow the contour of the component to be tested. This was not feasible in the prior art, since the known probes are too heavy and inflexible.

The sliding plate may have a recess on the top, in which the base body is received with pivot pins, so that the pivot pins and thus a rotational axis lies near to the lower surface of the sliding plate. A rotation is thereby achieved at a low center of gravity.

Through the enlarged sliding plate, which has a surface area that is larger in its dimensions than the size dimension of a through hole in the test direction of the component to be tested, the generation of a sustainable water cushion is promoted, so that the operation of the planar probe in connection with a gravitation-compensating device is possible. Thus, an advantage is achieved compared to the prior art, in that extensive components with, where applicable, uneven surface areas can be tested without expensive programming effort, since surface fluctuations can be compensated by the gravitation-compensating device.

In the case of an alternate embodiment, it is provided that the sidewalls of the probe arrangements may have moldings for the reception of pivot pins, which may be combined with the holding device of the probe arrangement around the X-axis. Thus, a rotational motion of the probe arrangement around the X-axis is made possible while a longitudinal movement is provided for in the Y-direction by the gravitation-compensating device.

The probe with the sliding plate may be floating over the component to be tested, and the lower surface of the sliding plate may be mounted on the existing water cushion.

What is claimed:

1. A probe arrangement for the coupling of ultrasonic signals to a planar component to be tested by water jet technology, the probe arrangement comprising:
    at least one preflow chamber with at least one water inlet;
    a flow chamber located downstream of at least one preflow chamber, wherein the flow chamber extends through a slot-shaped water outlet opening to a lower surface of the probe arrangement;
    a probe detachably arranged outside of at least one of the flow chamber and the at least one preflow chamber in a freely accessible manner, wherein a
    a base body for the reception of the probe; and
    a sliding plate comprising the slot-shaped water outlet opening, the sliding plate forming a lower surface of the probe arrangement on the component side, whose planar extension along the component is larger than the planar extension of the base body along the component,
    wherein a waterflow forms between the lower surface of the probe arrangement and a surface area of the component to be tested.

2. The probe arrangement according to claim 1, wherein the sliding plate has a length in a test direction of the component to be tested which is larger than the extension of a through hole present in the component in the test direction, and/or the sliding plate has a breadth transversely to the test direction of the component which is larger than the extension of one or each through hole transversely to the test direction.

3. The probe arrangement according to claim 1, wherein the sliding plate has a length in the range of 100 mm≤L≤200 mm, a breadth in the range of 200 mm≤B≤300 mm, and as thickness in the range of 5 mm≤D≤20 mm.

4. The probe arrangement according to claim 1, wherein the sliding plate has a length of 160 mm.

5. The probe arrangement according to claim 1, wherein the sliding plate has a breadth of 230 mm.

6. The probe arrangement according to claim 1, wherein the sliding plate comprises slot-shaped milled-out portions running in the test direction over the lower surface facing the component to be tested.

7. The probe arrangement according to claim 1, wherein the slot-shaped water outlet opening has a length transversely to the test direction in the range of 50 mm≤LS≤100 mm, and a breadth in the test direction in the range of 4 mm≤BS≤10 mm.

8. The probe arrangement according to claim 1, wherein the slot-shaped water outlet opening has a length transversely to the test direction of 75 mm.

9. The probe arrangement according to claim 1, wherein the slot-shaped water outlet opening has a breadth in the test direction of 6 mm.

10. The probe arrangement according to claim 1, further comprising additional water outlet openings arranged in the lower surface of the sliding plate, wherein the additional water outlet openings are connected with water supply conduits via the at least one prelim chamber.

11. The probe arrangement according to claim 1, wherein the base body is designed essentially in a U-shaped form and wherein the base body comprises a base plate from which short sidewall elements extend from opposite ends with respect to a length of the base plate,
    the base plate comprising:
        a slot-shaped opening along a longitudinal axis of the base plate configured to receive the lower surface of the probe; and
        through holes arranged on both sides of the slot-shaped opening,
    wherein the through holes extend to an upper surface of the base plate in the at least one preflow chamber, the through holes being connected with the at least one preflow chamber,
    wherein two flow chamber elements are arranged between the sidewall elements on a lower surface of the base plate along the longitudinal sides of the base plate forming an internal contour of the flow chamber, and
    wherein the two flow chamber elements can be fixed over the sliding plate running parallel to the base plate and can be fastened to the base body.

12. The probe arrangement according to claim 1, including two preflow chambers, wherein the probe is arranged between the two preflow chambers.

13. The probe arrangement according to claim 11, wherein the at least one preflow chamber is designed quadrangularly and comprises a plastic material, the at least one preflow chamber comprising a milling introduced on a lower surface of the at least one preflow chamber forming a chamber space, and further comprising connections introduced in an upper surface of the at least one preflow chamber for the reception of a water connection,
    wherein the at least one preflow chamber can be screwed in on the upper surface of the base plate via fastening elements, such that the through holes arranged on both sides of the slot-shaped opening open out into the chambers of the at least one preflow chamber.

14. The probe arrangement according to claim 11, wherein the through holes are mounted in an angle bracket in the base plate of the base body, which corresponds essentially to an angle of inclination of the flow chamber contour in the area of the through holes.

15. The probe arrangement according to claim 1, wherein the probe arrangement is arranged cardanically around a longitudinal axis of the probe arrangement and wherein the probe arrangement is swivel-mounted in a holding device.

16. The probe arrangement according claim 15, wherein the base body comprises receptacles for pivot pins with which the probe arrangement can be combined with the holding device.

17. The probe arrangement according to claim 16, wherein the sliding plate comprises a recess for reduction of a distance of the pivot pins to the lower surface of the sliding plate.

18. A device for the ultrasonic testing of a planar component by water jet technology, the device comprising:
a probe arrangement comprising:
at least one preflow chamber with at least one water inlet;
a flow chamber located downstream of at least one preflow chamber, wherein the flow chamber extends through a slot-shaped water outlet opening to a lower surface of the probe arrangement;
a probe detachably arranged outside of at least one of the flow chamber and the at least one preflow chamber in a freely accessible manner, wherein a lateral surface of the probe comprises emitting/receiving elements and forms an inner wall section of the flow chamber,
a base body for the reception of the probe; and
a sliding plate comprising the slot-shaped water outlet opening, the sliding plate forming as lower surface of the probe arrangement on a component side, whose planar extension along the component is larger than the planar extension of the base body along the component,
wherein a waterflow forms between the lower surface of the probe arrangement and a surface area of the component to be tested, and
wherein the probe arrangement can be combined with a handling machine via a holding device and swivel-mounted in the holding device around the axis running transversely to a test direction and wherein the probe arrangement can be moved along the component in the test direction,
wherein the sliding plate projects above a base area of the base body, and wherein the probe arrangement is adapted to glide on a water-sliding cushion formed between the lower surface of the sliding plate and a surface area of the component.

19. The device according to claim 18, wherein at least one section of the lower surface of the sliding plate bears on the surface area of the component when the sliding plate is run over the component to be tested.

* * * * *

UNITED STATES PATENT AND TRADEMARK OFFICE
CERTIFICATE OF CORRECTION

| | |
|---|---|
| PATENT NO. | : 8,650,959 B2 |
| APPLICATION NO. | : 13/127430 |
| DATED | : February 18, 2014 |
| INVENTOR(S) | : De Odorico et al. |

Page 1 of 1

It is certified that error appears in the above-identified patent and that said Letters Patent is hereby corrected as shown below:

In the Specification

In Column 2, Line 43, delete "farmed" and insert -- formed --, therefor.

In Column 6, Line 14, delete "sealable" and insert -- scalable --, therefor.

In the Claims

In Column 7, Line 34, in Claim 1, delete "wherein a" and insert -- wherein --, therefor.

In Column 7, Line 53, in Claim 3, delete "and as" and insert -- and a --, therefor.

In Column 8, Line 11, in Claim 10, delete "prelim" and insert -- preflow --, therefor.

In Column 9, Line 16, in Claim 18, delete "forming as lower" and insert -- forming a lower --, therefor.

Signed and Sealed this
Tenth Day of June, 2014

Michelle K. Lee
*Deputy Director of the United States Patent and Trademark Office*